(12) United States Patent
Furukawa et al.

(10) Patent No.: US 7,067,692 B2
(45) Date of Patent: Jun. 27, 2006

(54) PRODUCTION METHOD OF ADAMANTYL ACRYLATE COMPOUNDS

(75) Inventors: Kikuo Furukawa, Ibaraki (JP); Minoru Kakuda, Chiba (JP); Yoshio Nishimura, Ibaraki (JP); Takehiko Isobe, Ibaraki (JP); Mitsuharu Suzuki, Ibaraki (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 227 days.

(21) Appl. No.: 10/825,118

(22) Filed: Apr. 16, 2004

(65) Prior Publication Data

US 2004/0210082 A1 Oct. 21, 2004

(30) Foreign Application Priority Data

Apr. 18, 2003 (JP) .............................. 2003-113990

(51) Int. Cl.
*C00C 67/26* (2006.01)
(52) U.S. Cl. ....................................... 560/220
(58) Field of Classification Search ................. 560/220
See application file for complete search history.

(56) References Cited

U.S. PATENT DOCUMENTS 6,521,781 B1 * 2/2003 Kakuda et al. ............. 560/220

FOREIGN PATENT DOCUMENTS

| EP | 1 283 198 | | 2/2003 |
| JP | 56-36433 | | 4/1981 |
| JP | 2003-12579 | | 1/2003 |
| JP | 2003012579 | * | 1/2003 |
| JP | 2004-91402 | | 3/2004 |
| WO | WO 02/100816 | | 12/2002 |
| WO | WO 2002100816 | * | 12/2002 |

OTHER PUBLICATIONS

Communication with European Search Report dated Sep. 6, 2004, for No. EP 04 00 8690.

* cited by examiner

*Primary Examiner*—Johanna Richter
*Assistant Examiner*—Chukwuma Nwaonicha
(74) *Attorney, Agent, or Firm*—Antonelli, Terry, Stout and Kraus, LLP.

(57) ABSTRACT

In the present invention, an adamantyl acrylate compound is produced by a process comprising a first step and a second step without using acid halide. In the first step, a 2-adamantanone compound is reacted with a hydrocarbyl halide in the presence of lithium metal to form an adamantanolate intermediate that is then reacted with an acrylic ester compound in the second step to produce the aimed adamantyl acrylate compound.

7 Claims, No Drawings

PRODUCTION METHOD OF ADAMANTYL ACRYLATE COMPOUNDS

BACKGROUND OF THE INVENTION

1. Field of the Invention

The present invention relates to a method of producing adamantyl acrylate compounds which attract attention as the raw materials of resists for KrF, ArF, or $F_2$ excimer laser, resists for X ray, electron beam or extreme ultraviolet (EUV), high performance polymers, etc.

2. Description of the Prior Art

In the general production of 2-alkyl-2-adamantyl (meth)acrylates from a 2-adamantanone derivative corresponding to their ester moiety, the 2-adamantanone derivative is converted into a 2-alkyl-2-adamantanol derivative and then the 2-alkyl-2-adamantanol derivative is allowed to react with (meth)acryloyl halide, etc.

K. Nozaki et al., Jpn. J. Appl. Phys. 35, 528 (1996) discloses the production of 2-methyl-2-adamantyl methacrylate by the esterification between 2-methyl-2-adamantanol and methacryloyl chloride. Japanese Patent Application Laid-Open No. 2000-229911 discloses the production of 2-alkyl-2-adamantyl (meth)acrylate by the reaction of a corresponding 2-alkyl-2-adamantanol derivative and (meth)acryloyl chloride. In the method disclosed in Japanese Patent Application Laid-Open No. 2000-309558, a corresponding 2-alkyl-2-adamantanol derivative or its metal salt is reacted with (meth)acryloyl halide.

Japanese Patent Application Laid-Open No. 10-182552 discloses the production method of a tertiary alcohol ester of carboxylic acid (for example, adamantyl ester of carboxylic acid) by reacting a ketone compound (for example, 2-adamantanone) with a carboxylic acid halide in the presence of an organometallic compound without separating and purifying the tertiary alcohol derived from the ketone compound.

In the methods disclosed in WO 01/87817 and Japanese Patent Application Laid-Open No. 2003-73334, 2-adamantanone and an alkyl halide dissolved or dispersed in a solvent are reacted in the presence of lithium metal into lithium 2-alkyl-2-adamantanolate that is then reacted with methacryloyl halide, thereby producing a 2-alkyl-2-adamantyl methacrylate.

These methods, however, involve drawbacks of using the expensive (meth)acryloyl halide as the esterifying agent which is difficult to handle and generates a large amount of by-products difficult to remove. The use of the (meth)acryloyl halide by-produces alkyladamantyl halide that generates acid during the purification by distillation to decompose the aimed 2-alkyl-2-adamantyl (meth)acrylate and significantly reduce its yield.

Japanese Patent Application Laid-Open No. 2001-97924 proposes a method for preventing the reduction of yield, wherein a mixture of alkyladamantyl halide and a 2-alkyl-2-adamantyl (meth)acrylate is contacted with an alkali compound to convert the alkyladamantyl halide into a compound not generating acid during the purification by distillation. In addition, Japanese Patent Application Laid-Open No. 2000-229911 proposes a method for producing a 2-alkyl-2-adamantyl (meth)acrylate in high yields by using acid chloride prepared by the reaction of benzoyl chloride or phosphorus trichloride with (meth)acrylic acid. However, since the use of acid halide requires a specific means, it has been demanded to develop an industrially easy-to-practice method of producing the adamantyl acrylate compound in high yields without using acid halide.

In the method of Japanese Patent Application Laid-Open No. 2002-241342, a 2-adamantanone compound is reacted with a (meth)acrylic ester or a (meth)acrylic anhydride in the presence of an organometallic compound. In this method, the adamantyl (meth)acrylate compound is produced in a sufficiently high yield. However, to produce the aimed adamantyl acrylate compound, it is needed to prepare an organometallic agent such as alkyllithium and alkylmagnesium halide in advance, making the production process long. Some of the organometallic agents result in poor yields and some are poor in storing stability. This makes the industrial production thereof difficult in some cases.

SUMMARY OF THE INVENTION

An object of the present invention is to provide a production method of an adamantly acrylate compound from a 2-adamantanone compound without using (meth)acryloyl halide which does not need the preparation of an organometallic agent in advance and which is highly simplified in its production steps.

As a result of extensive research in view of the above object, the inventors have found a production method which is capable of efficiently producing the adamantly acrylate compound from the 2-adamantanone compound by production steps simplified as compared with known methods.

Thus, the present invention provides a method for producing an adamantyl acrylate compound represented by the following formula (4):

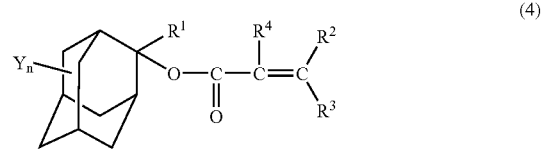

wherein Y is hydrogen atom or alkyl group; $R^1$ is hydrocarbyl group; each of $R^2$ to $R^4$ is independently hydrogen atom, alkyl group, halogen atom or haloalkyl group; and n is an integer of 1 to 14, the method comprising a first step of reacting a 2-adamantanone compound represented by the following formula (1):

wherein Y and n are the same as defined above, with a hydrocarbyl halide represented by the following formula (2):

wherein $R^1$ is the same as defined above and X is halogen atom, in the presence of lithium metal; and a second step of further continuing the reaction after adding an acrylic ester compound into a reaction system, the acrylic ester compound being represented by the following formula (3):

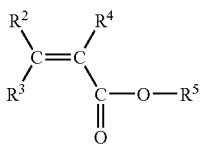

wherein $R^2$ to $R^4$ are the same as defined above and $R^5$ is alkyl group.

DETAILED DESCRIPTION OF THE INVENTION

The production method of the adamantyl acrylate compound comprises a first step of reacting the 2-adamantanone compound with the hydrocarbyl halide in the presence of lithium metal, and a second step of further continuing the reaction after adding the acrylic ester compound into the reaction system.

The 2-adamantanone compound (2-adamantanone and its derivatives) used as the starting compound in the present invention is represented by the following formula (1):

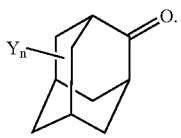

In the formula (1), Y is hydrogen atom or alkyl group. Preferred alkyl groups are those having 1 to 10 carbon atoms such as methyl group, ethyl group, isopropyl group and amyl group. The subscript "n" is an integer of 1 to 14. A plurality of Y groups, when n is 2 to 14, may be the same or different. 2-Adamantanone is particularly preferable as the 2-adamantanone compound.

In the method of the present invention, lithium metal may be in the form of granule, flake, fine particle, ribbon, lump, etc. It is preferred for lithium metal to have a larger surface area because the reaction rate is higher and the control of the reaction is easier. In view thereof, it is preferred to use particulate lithium metal having a particle size of 1000 μm or less, preferably 10 to 1000 μm. In the method of the present invention, such particulate lithium metal is prepared in advance and charged into a reactor for the reaction. Alternatively, lithium metal in the form of lump, etc. having a smaller surface area may be made into particulate lithium metal in a reactor by dispersed throughout an inert solvent such as paraffin at high temperatures, and then, used in the reaction.

The amount of lithium metal to be used is preferably 1 to 5 equivalents, more preferably 1.8 to 2.4 equivalents based on the starting 2-adamantanone compound. If less than the above range, the starting 2-adamantanone compound remains unchanged. The use of an amount exceeding the above range only results in the increased amount of remaining lithium metal and the reduction of yield.

In the formula (2) representing the alkyl halide:

$$R^1X \quad (2),$$

$R^1$ is a hydrocarbyl group, preferably an aliphatic, alicyclic or aromatic hydrocarbon group having 1 to 10 carbon atoms, more preferably methyl group, ethyl group, propyl group and butyl group. X is a halogen such as chlorine, bromine and iodine. Examples of the alkyl halides include methyl bromide, ethyl bromide, butyl bromide, methyl iodide, ethyl iodide, butyl iodide, methyl chloride, ethyl chloride, and butyl chloride.

The amount of the hydrocarbyl halide to be used is preferably 1 to 10 equivalents, more preferably 1 to 1.2 equivalents based on the starting 2-adamantanone compound. If exceeding the above range, the hydrocarbyl lithium reagent is produced in a larger amount by the contact between the hydrocarbyl halide and lithium metal, and the excess thereof polymerizes the acrylic ester compound which is to be added in a later stage of the method to reduce the yield of the aimed adamantyl acrylate compound.

The reaction of the first step is conducted either in the presence or absence of a solvent, preferably in the presence of a solvent. Examples of the solvents include ethers such as tetrahydrofuran and diethyl ether; aliphatic hydrocarbons such as hexane, heptane and cyclohexane; and aromatic hydrocarbons such as benzene, toluene and cumene, although not specifically limited thereto as far as inert to the reaction. The amount of the solvent to be used is preferably 1 to 50 mL per one gram of the 2-adamantanone compound.

The starting material, etc. are not necessarily completely dissolved in the solvent and the reaction may be conducted in a slurry condition as far as the stirring is not adversely affected. In addition, the reaction solution may change from solution state to slurry state and vice versa with the progress of the reaction as far as having no adverse influence on the production process. In the present invention, the term "solution" also includes slurry for simplification of description.

The 2-adamantanone compound, the hydrocarbyl halide and lithium metal may be mixed in any manner without specific limitation. The 2-adamantanone compound and the hydrocarbyl halide may be dissolved in the solvent in advance, and then, lithium metal may be added. Alternatively, the hydrocarbyl halide and lithium metal may be first reacted with each other in the solution, and then, the 2-adamantanone compound may be added. The addition may be carried out at once or successively. Although the addition speed is not critical, it is generally preferred to add in a speed not to cause abnormal rise of the reaction temperature.

The reaction temperature of the first step is −70 to 200° C., preferably −50 to 100° C. If less than −70° C., the reaction rate is low. If exceeding 200° C., the control of the reaction becomes difficult and the yield is reduced because of the progress of side reaction. The reaction temperature of the first step may be changed within the range of −70 to 200° C. by heating or cooling.

In the first step, the 2-adamantanone compound is converted into a reaction intermediate, lithium 2-hydrocarbyl-2-adamantanolate. In the present invention, the acrylic ester compound is added to the reaction system preferably without separating the reaction intermediate to conduct the reaction (esterification) of the second step.

The acrylic ester compound is represented by the following formula (3):

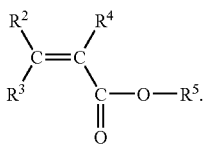

(3)

In the formula (3), $R^2$ to $R^4$ are each independently hydrogen atom, halogen atom, alkyl group or haloalkyl group. Examples of alkyl groups include those having 1 to 4 carbon atoms such as methyl group and ethyl group. The halogen may include fluorine. The haloalkyl group may include alkyl groups having 1 to 4 carbon atoms which are partially or fully substituted with halogen, for example, trifluoromethyl group. Preferred as $R^2$ to $R^4$ is hydrogen atom, fluorine atom, methyl group and trifluoromethyl group.

$R^5$ is alkyl, preferably alkyl having 1 to 6 carbon atoms such as methyl and ethyl. Examples of the acrylic ester compounds include methyl acrylate, ethyl acrylate, isopropyl acrylate, methyl methacrylate, ethyl methacrylate, isopropyl methacrylate, methyl trifluoroacrylate, ethyl trifluoroacrylate, isopropyl trifluoroacrylate, t-butyl trifluoroacrylate, methyl pentafluoromethacrylate, ethyl pentafluoromethacrylate, isopropyl pentafluoromethacrylate, t-butyl pentafluoromethacrylate, methyl 2-fluoroacrylate, ethyl 2-fluoroacrylate, isopropyl 2-fluoroacrylate, t-butyl 2-fluoroacrylate, methyl 2-(trifluoromethyl)acrylate, ethyl 2-(trifluoromethyl)acrylate, isopropyl 2-(trifluoromethyl)acrylate, and t-butyl 2-(trifluoromethyl)acrylate.

The amount of the acrylic ester compound to be added is 1 to 100 equivalents, preferably 1 to 20 equivalents based on the starting 2-adamantanone compound. If less than one equivalent, the yield is reduced, and the reactor efficiency is reduced and the purification becomes difficult if exceeding 100 equivalents.

The addition method and the addition speed of the acrylic ester compound are not specifically limited. Generally, the acrylic ester compound is added to the reaction system preferably after the starting 2-adamantanone compound is sufficiently converted into the intermediate lithium 2-hydrocarbyl-2-adamantanolate, more preferably after the conversion reaches at least 80 mol %.

It is not always required to isolate lithium 2-hydrocarbyl-2-adamantanolate before adding the acrylic ester compound. The remaining lithium metal may be separated from lithium 2-hydrocarbyl-2-adamantanolate or not. If substantially no lithium metal remains, the acrylic ester compound may be directly added.

In the present invention, the use of an optional polymerization inhibitor having nitroso group is effective. Particularly effective for inhibiting polymerization are 2,2,6,6-tetramethyl-4-hydroxypiperidine-1-oxyl, N-nitrosophenyl hydroxylamine ammonium salt, N-nitrosophenyl hydroxylamine aluminum salt, N-nitroso-N-(1-naphthyl) hydroxylamine ammonium salt, N-nitrosodiphenylamine and N-nitroso-N-methylaniline.

The effect of inhibiting polymerization can be enhanced in some cases when an auxiliary polymerization inhibitor is combinedly used in addition to the above polymerization inhibitor. Examples of the auxiliary polymerization inhibitors include nitroso compounds such as nitrosonaphthol, p-nitrosophenol and N,N'-dimethyl-p-nitrosoaniline; sulfur-containing compounds such as phenothiazine, Methylene Blue and 2-mercaptobenzimidazole; amines such as N,N'-diphenyl-p-phenylenediamine, N-phenyl-N'-isopropyl-p-phenylenediamine, 4-hydroxydiphenylamine and aminophenol; quinone compounds such as hydroxyquinoline, hydroquinone, methylhydroquinone, p-benzoquinone and hydroquinone monomethyl ether; phenol compounds such as methoxyphenol, 2,4-dimethyl-6-t-butylphenol, catechol, 3-s-butylcatechol and 2,2-methylenebis-(6-t-butyl-4-methylphenol); imides such as N-hydroxyphthalimide; oximes such as cyclohexane oxime and p-quinone dioxime; and dialkylthio dipropionates. The auxiliary polymerization inhibitor alone is little effective for inhibiting polymerization.

The amount of the polymerization inhibitor to be added is 0.00001 to 0.1 part by weight, preferably 0.0001 to 0.02 part by weight based on one part by weight of the acrylic acid compound. If less than the above range, no effect of inhibiting polymerization is obtained, and the effect of inhibiting polymerization is no longer enhanced if exceeding the above range.

The addition method and the addition speed of the polymerization inhibitor are not specifically limited. Generally, the polymerization inhibitor is preferably added at the same time with, just before or immediately after the addition of the acrylic ester compound. The polymerization inhibitor may be added in the form of solution in the acrylic ester compound or may be added separately through a feed port which is different from a feed port for the acrylic ester compound. In addition, the polymerization inhibitor may be added directly or in the form of solution in the solvent.

The reaction temperature of the second step is preferably −70 to 200° C., more preferably −50 to 100° C. If less than −70° C., the reaction rate is low. If exceeding 200° C., the control of the reaction becomes difficult and the yield is reduced because of the progress of side reaction. The reaction temperature of the second step may be the same as or different from the reaction temperature of the first step, and may be changed within the range of −70 to 200° C. by heating or cooling.

The reaction time of the second step (esterification) is preferably 0.5 to 1000 h, more preferably 1 to 100 h, although not limited thereto because the reaction time depends on the reaction temperature and is determined according to the intended yield, etc.

After completing the reaction, the non-reacted lithium metal and the lithium salt derived from the hydrocarbyl lithium are removed by washing the reaction solution with water. The washing water may contain a suitable inorganic salt such as sodium chloride and sodium hydrogencarbonate. In addition, impurities may be removed by alkali washing using an aqueous sodium hydroxide solution, an aqueous potassium hydroxide solution, aqueous ammonia, etc., although the alkali component is not limited thereto. To remove metallic impurities, the reaction solution may be washed with acid using an aqueous solution of inorganic acid such as hydrochloric acid, sulfuric acid and phosphoric acid or organic acid such as oxalic acid. Since a trace amount of hydrochloric acid may decompose the aimed compound during the purification by distillation, it is generally preferred to use the inorganic acid other than hydrochloric acid.

Before washing, an organic solvent may be added to the reaction solution according to the properties of the produced adamantyl acrylate compound. The organic solvent to be added may be the same or different from the reaction solvent. Generally, a solvent with a small polarity is preferably used because of its easy separation from water.

In addition, to remove discolored substances and polymeric products, the reaction solution may be subjected to a known treatment such as activated carbon treatment and adsorption treatment with silica gel.

The adamantyl acrylate compound thus obtained is separated from the organic phase and purified by a known method such as distillation, concentration, filtration, crystallization, recrystallization, and column chromatography.

The present invention will be described in further detail by way of the following examples which are not intended to limit the scope of the present invention thereto.

EXAMPLE 1

Under argon atmosphere, 4.6 g of lithium metal and 500 mL of tetrahydrofuran (THF) were charged into a 2-L three-necked flask. Separately, 50 g of 2-adamantanone and 44 g of ethyl bromide were dissolved in 500 mL of THF under nitrogen atmosphere. Then, the 2-adamantanone/ethyl bromide solution was added dropwise to the three-necked flask, while maintaining the solution temperature in the flask at 30 to 40° C. After completing the dropwise addition, the reaction mixture was kept stand. When the conversion of 2-adamantanone into lithium 2-ethyl-2-adamantanolate (detected as 2-ethyl-2-adamantanol in gas chromatographic analysis) was confirmed to reach 98 mol % under gas chromatography, 167 g of methyl methacrylate was slowly added dropwise and then 0.3 g of N-nitrosophenyl hydroxylamine ammonium salt was added. Then the flask was immersed in a silicone bath to allow the reaction to proceed for 7 h at 60° C.

After completing the reaction, the reaction solution was successively added with 250 mL of hexane and 250 mL saturated aqueous solution of sodium chloride, and then stirred thoroughly. After liquid-liquid separation of the reaction solution, the organic layer was washed twice with 200 mL of pure water. The solvent and the non-reacted methyl methacrylate were removed by concentrating the organic layer to obtain a crude product, which was then purified by distillation and crystallization to obtain 58 g (70% yield) of pure 2-ethyl-2-adamantyl methacrylate when determined by GC-MS analysis and $^1$H NMR analysis.

EXAMPLE 2

Under argon atmosphere, 4.6 g of lithium metal and 500 mL of THF were charged into a 2-L three-necked flask. Separately, 50 g of 2-adamantanone and 44 g of ethyl bromide were dissolved in 500 mL of THF under nitrogen atmosphere. Then, the 2-adamantanone/ethyl bromide solution was added dropwise to the three-necked flask, while maintaining the solution temperature in the flask at 30 to 40° C. After completing the dropwise addition, the reaction mixture was kept stand. When the conversion of 2-adamantanone into lithium 2-ethyl-2-adamantanolate (detected as 2-ethyl-2-adamantanol in gas chromatographic analysis) was confirmed to reach 98 mol % under gas chromatography, 167 g of methyl methacrylate was slowly added dropwise and then 0.3 g of N-nitrosophenyl hydroxylamine ammonium salt was added. Then the flask was immersed in a silicone bath to allow the reaction to proceed for 7 h at 60° C.

After completing the reaction, the reaction solution was successively added with 250 mL of hexane and 250 mL pure water, and then stirred thoroughly. After liquid-liquid separation of the reaction solution, the organic layer was washed twice with 250 mL of pure water. The solvent and the non-reacted methyl methacrylate were removed by concentrating the organic layer to obtain a crude product (75% yield). The polymeric products were re-precipitated by adding hexane to the crude product and removed by suction filtration. The crude product was further subjected to silica gel treatment, concentration and crystallization from acetonitrile to obtain 50 g (60% yield) of 2-ethyl-2-adamatyl methacrylate having a purity of 99% or more when determined by GC-MS analysis and $^1$H NMR analysis.

According to the present invention, since the esterification reaction proceeds nearly quantitatively, a highly pure adamantyl acrylate compound is produced in high yields by a simple production process without using acid halide.

What is claimed is:

1. A method for producing an adamantyl acrylate compound represented by the following formula (4):

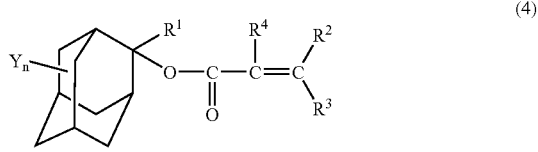

(4)

wherein Y is hydrogen atom or alkyl group; $R^1$ is hydrocarbyl group; each of $R^2$ to $R^4$ is independently hydrogen atom, alkyl group, halogen atom or haloalkyl group; and n is an integer of 1 to 14, the method comprising a first step of reacting a 2-adamantanone compound represented by the following formula (1):

(1)

wherein Y and n are the same as defined above,
with an alkyl halide represented by the following formula (2):

$$R^1X \qquad (2)$$

wherein $R^1$ is the same as defined above and X is halogen atom, in the presence of lithium metal; and a second step of further continuing the reaction after adding an acrylic ester compound into a reaction system, the acrylic ester compound being represented by the following formula (3):

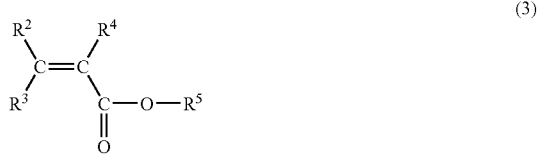

(3)

wherein $R^2$ to $R^4$ are the same as defined above and $R^5$ is alkyl group.

2. The method according to claim 1, wherein the second step is conducted in the presence of a polymerization inhibitor.

3. The method according to claim 2, wherein the polymerization inhibitor has a nitroso group.

4. The method according to claim 3, wherein the polymerization inhibitor having a nitroso group is at least one compound selected from the group consisting of 2,2,6,6-tetramethyl-4-hydroxypiperidine-1-oxyl, N-nitrosophenyl hydroxylamine ammonium salt, N-nitrosophenyl hydroxylamine aluminum salt, N-nitroso-N-(1-naphthyl)hydroxylamine ammonium salt, N-nitrosodiphenylamine and N-nitroso-N-methylaniline.

5. The method according to claim 2, wherein the polymerization inhibitor is used in an amount of 0.00001 to 0.1 part by weight per one part by weight of the acrylic ester compound of the formula (3).

6. The method according to claim 1, wherein the 2-adamantanone compound of the formula (1) is 2-adamantanone.

7. The method according to claim 1, wherein a particle size of lithium metal is 1000 μm or less.

* * * * *